US012667732B2

(12) United States Patent
Shalev et al.

(10) Patent No.: US 12,667,732 B2
(45) Date of Patent: Jun. 30, 2026

(54) PULSED ELECTROMAGNETIC FIELD TRANSMISSION FOR NANOPARTICLES

(71) Applicant: NEW PHASE LTD., Petah Tikva (IL)

(72) Inventors: Boaz Shay Shalev, Kfar Sava (IL); Doron Suchi, Bahan (IL); Ofer Shalev, Kfar Sava (IL); Moshe Eltanani, Kfar Sava (IL); Michal Eck, Kiryat Ono (IL); Sarah Kraus, Rishon LeZion (IL)

(73) Assignee: NEW PHASE LTD., Petah Tikva (IL)

( * ) Notice: Subject to any disclaimer, the term of this patent is extended or adjusted under 35 U.S.C. 154(b) by 0 days.

(21) Appl. No.: 19/350,504

(22) Filed: Oct. 6, 2025

(65) Prior Publication Data

US 2026/0097223 A1     Apr. 9, 2026

Related U.S. Application Data

(60) Provisional application No. 63/705,326, filed on Oct. 9, 2024.

(51) Int. Cl.
*A61N 1/40*        (2006.01)
*A61K 9/51*        (2006.01)
*A61K 41/00*       (2020.01)

(52) U.S. Cl.
CPC ............ *A61N 1/406* (2013.01); *A61K 9/5146* (2013.01); *A61K 41/0052* (2013.01)

(58) Field of Classification Search
CPC ............................ A61N 1/406; A61K 41/0052
See application file for complete search history.

(56) References Cited

U.S. PATENT DOCUMENTS 3,915,151  A     10/1975   Kraus
4,066,065  A      1/1978   Kraus
7,510,555  B2     3/2009   Kanzius
8,019,414  B2     9/2011   Palti
        (Continued)

FOREIGN PATENT DOCUMENTS

CA         2042968  A1    11/1991
CN        104127872  A    11/2014
        (Continued)

OTHER PUBLICATIONS

Machine Translation of KR 20180002233 A (Year: 2018).*
        (Continued)

*Primary Examiner* — Kaitlyn E Smith
(74) *Attorney, Agent, or Firm* — Sughrue Mion, PLLC

(57)         ABSTRACT

A system is provided for use with a subject suffering from cancer that includes one or more primary or metastatic solid tumors. The system includes nanoparticles including a magnetic metallic core and a phase-change material (PCM) that surrounds the magnetic metallic core and is configured to absorb latent heat of fusion by undergoing a phase change that occurs at a phase-change temperature of 42-80 degrees C. A radiofrequency (RF) transmitter is configured to transmit energy, in a pulse train alternating between high power and low power at a pulse frequency of 1 Hz-5 Hz, to at least a portion of the subject's body, such so that the nanoparticles are heated to the phase-change temperature of the PCM, and store energy from the pulse train in the PCM as latent heat of fusion. Other embodiments are also described.

22 Claims, 4 Drawing Sheets

(56) References Cited

U.S. PATENT DOCUMENTS

| | | | |
|---|---|---|---|
| 9,572,695 B2 | 2/2017 | Hof et al. | |
| 9,872,902 B2 | 1/2018 | Hof et al. | |
| 2005/0090732 A1 | 4/2005 | Ivkov et al. | |

FOREIGN PATENT DOCUMENTS

| | | | | | |
|---|---|---|---|---|---|
| EP | 0039988 A1 | | 11/1981 | | |
| EP | 0543498 A1 | | 5/1993 | | |
| KR | 20180002233 A | * | 1/2018 | ........... | A61K 31/155 |
| WO | WO-2015161211 A1 | * | 10/2015 | ............. | A61N 1/406 |
| WO | WO-2018154566 A1 | * | 8/2018 | ............. | A61P 35/00 |
| WO | 2021237360 A1 | | 12/2021 | | |
| WO | 2025088597 A1 | | 5/2025 | | |

OTHER PUBLICATIONS

Robert Ivkov, et al., "Application of High Amplitude Alternating Magnetic Fields for Heat Induction of Nanoparticles Localized in Cancer", Clinical Cancer Research, 2005, vol. 11, 19 Suppl., pp. 7093s- 7103s (12 pages total).

Sarah Kraus, et al., "Novel Nanoparticle-Based Cancer Treatment, Effectively Inhibits Lung Metastases and Improves Survival in a Murine Breast Cancer Model", Frontiers in Oncology, Nov. 2021, vol. 11, Article 761045, pp. 1-16.

Sarah Kraus, et al., "Self-regulating novel iron oxide nanoparticle-based magnetic hyperthermia in swine: biocompatibility, biodistribution, and safety assessments", Archives of Toxicology, 2022, vol. 96, No. 9, pp. 2447-2464 (18 pages total).

Aikaterini-Rafailia Tsiapla, et al., "Mitigation of magnetic particle hyperthermia side effects by magnetic field controls", International Journal of Hyperthermia, 2021, vol. 38, No. 1, pp. 511-522(13 pages total).

\* cited by examiner

PULSED ELECTROMAGNETIC FIELD TRANSMISSION FOR NANOPARTICLES

CROSS-REFERENCE TO RELATED APPLICATIONS

The present patent application claims priority from U.S. Provisional Application 63/705,326, filed Oct. 9, 2024, which is assigned to the assignee of the present application and incorporated herein by reference.

FIELD OF THE INVENTION

The present invention relates generally to treatment of solid tumors, and specifically to treatment of primary and metastatic solid tumors using nanoparticles containing a magnetic metallic core.

BACKGROUND OF THE INVENTION

Magnetic nanoparticle-based hyperthermia is a method of treating cancer, in which heat is applied to cancer tissues by magnetic nanoparticles in order to kill cancer cells within the tissues.

The electromagnetic (EM) field is a key element in the success of the treatment of magnetic nanoparticle-based hyperthermia. The emitted EM field passes through the patient's body and is absorbed by the magnetic nanoparticles, causing them to heat up and in turn to apply heat to the cancer tissue.

Magnetic nanoparticle-based hyperthermia may use, for example, nanoparticles that comprise a phase-change material (PCM) layer surrounding a magnetic metallic core. For example, the magnetic metallic core may comprise iron oxide nanoparticles. Some suitable nanoparticles are described in the following references, all of which are incorporated herein by reference:

PCT Publication WO 2025/088597 to Kraus et al.

Kraus S et al., "Novel Nanoparticle-Based Cancer Treatment, Effectively Inhibits Lung Metastases and Improves Survival in a Murine Breast Cancer Model," Front Oncol. 2021 Nov. 5; 11:761045.

Kraus S et al., "Self-regulating novel iron oxide nanoparticle-based magnetic hyperthermia in swine: biocompatibility, biodistribution, and safety assessments," Arch Toxicol. 2022 September; 96(9):2447-2464.

These nanoparticles rely on the following properties of PCMs. When a solid material is heated until its melting point, the material undergoes a phase change to its liquid state. During the phase change, the material accumulates a certain amount of heat, which is called the latent heat of fusion, or the enthalpy change of fusion. The temperature of the material stays relatively constant when the phase change occurs.

The transmitted EM field induces eddy currents on the patient's body circumference which leads to unwanted heating of the outer tissues. This parasitic heating, referred to as the Specific Absorption Rate (SAR), is proportional to the square of the average field power.

U.S. Pat. No. 9,872,902 to Hof et al. describes apparatus and methods for use with a subject suffering from cancer. A nanoparticle includes an inner core that comprises a PCM that is configured to absorb latent heat of fusion by undergoing a phase change. An outer layer disposed around the inner core includes a plurality of nano-spheres of at least one metal, and a plurality of molecules of a substance that binds preferentially with cancerous cells relative to non-cancerous cells. The nanoparticle has a volume of at least 65,000 nm3 and is elongatable into an ellipsoid, such that, when the nanoparticle is maximally elongated, each of the semi-axes defined by the ellipsoid is greater than 5 nm, and at least two of the semi axes of the ellipsoid are less than 30 nm. Other applications are also described.

U.S. Pat. No. 7,510,555 to Kanzius describes a method of inducing hyperthermia in at least a portion of a target area—e.g., a tumor or a portion of a tumor or targeted cancerous cells. Targeted RF absorption enhancers, e.g., antibodies bound to RF absorbing particles, are introduced into a patient. These targeted RF absorption enhancers will target certain cells in the target areas and enhance the effect of a hyperthermia generating RF signal directed toward the target area. The targeted RF absorption enhancers may, in a manner of speaking, add one or more RF absorption frequencies to cells in the target area, which will permit a hyperthermia generating RF signal at that frequency or frequencies to heat the targeted cells.

The above-cited paper by Kraus S et al., "Novel Nanoparticle-Based Cancer Treatment, Effectively Inhibits Lung Metastases and Improves Survival in a Murine Breast Cancer Model," Front Oncol. 2021 Nov. 5; 11:761045, describes Sarah Nanoparticles (SaNPs) as unique multicore iron oxide-based nanoparticles, developed for the treatment of advanced cancer, following standard care, through the selective delivery of thermal energy to malignant cells upon exposure to an alternating magnetic field. For their therapeutic effect, SaNPs need to accumulate in the tumor. Since the potential accumulation and associated toxicity in normal tissues are an important risk consideration, biodistribution and toxicity were assessed in naïve BALB/c mice. Therapeutic efficacy and the effect on survival were investigated in the 4T1 murine model of metastatic breast cancer. Toxicity evaluation at various timepoints did not reveal any abnormal clinical signs, evidence of alterations in organ function, nor histopathologic adverse target organ toxicity, even after a follow up period of 25 weeks, confirming the safety of SaNP use. The biodistribution evaluation, following SaNP administration, indicated that SaNPs accumulate mainly in the liver and spleen. A comprehensive pharmacokinetics evaluation, demonstrated that the total percentage of SaNPs that accumulated in the blood and vital organs was ~78%, 46%, and 36% after 4, 13, and 25 weeks, respectively, suggesting a time-dependent clearance from the body. Efficacy studies in mice bearing 4T1 metastatic tumors revealed a 49.6% and 70% reduction in the number of lung metastases and their relative size, respectively, in treated vs. control mice, accompanied by a decrease in tumor cell viability in response to treatment. Moreover, SaNP treatment followed by alternating magnetic field exposure significantly improved the survival rate of treated mice compared to the controls. The median survival time was 29±3.8 days in the treated group vs. 21.6±4.9 days in the control, p-value 0.029. These assessments open new avenues for generating SaNPs and alternating magnetic field application as a potential novel therapeutic modality for metastatic cancer patients.

Tsiapla A R et al., "Mitigation of magnetic particle hyperthermia side effects by magnetic field controls," Int J Hyperthermia. 2021; 38(1):511-522, provide the following Abstract: "Objective: In magnetic particle hyperthermia, a promising least-invasive cancer treatment, malignant regions in proximity with magnetic nanoparticles undergo heat stress, while unavoidably surrounding healthy tissues may also suffer from heat either directly or indirectly by the induced eddy currents, due to the developed electric fields as well. Here, we propose a facile upgrade of a typical magnetic particle hyperthermia protocol, to selectively mitigate eddy currents' heating without compromising the beneficial role of heating in malignant regions. Method: The key idea is to apply the external magnetic field intermittently (in an ON/OFF pulse mode), instead of the continuous field mode typically applied. The parameters of the intermittent field mode, such as time intervals (ON time: 25-100 s, OFF time: 50-200 s, Duty Cycle: 16-100%) and field amplitude (30-70 mT) are optimized based on evaluation on healthy tissue and cancer tissue phantoms. The goal is to sustain in cancer tissue phantom the maximum temperature increase (preferably within 4-8° C. above body temperature of 37° C.), while in the healthy tissue phantom temperature variation is suppressed far below the 4° C. dictating the eddy current mitigation. Results: Optimum conditions of intermittent field (ON/OFF: 50/100 in s, Duty Cycle: 33%, magnetic field: 45 mT) are then examined in ex-vivo samples verifying the successful suppression of eddy currents. Simultaneously, a well-elaborated theoretical approach provides a rapid calculation of temperature increase and, furthermore, the ability to quickly simulate a variety of duty cycle times and field controls may save experimental time. Conclusion: Eventually, the application of an intermittent field mode in a magnetic particle hyperthermia protocol, succeeds in eddy current mitigation in surrounding tissues and allows for the application of larger field amplitudes that may augment hyperthermia efficiency without objecting typical biomedical applicability field constraints such as Brezovich criterion."

Ivkov R et al., "Application of high amplitude alternating magnetic fields for heat induction of nanoparticles localized in cancer," Clin Cancer Res. 2005 Oct. 1; 11(19 Pt 2): 7093s-7103s, provide the following Abstract: "Objective: Magnetic nanoparticles conjugated to a monoclonal antibody can be i.v. injected to target cancer tissue and will rapidly heat when activated by an external alternating magnetic field (AMF). The result is necrosis of the microenvironment provided the concentration of particles and AMF amplitude are sufficient. High-amplitude AMF causes non-specific heating in tissues through induced eddy currents, which must be minimized. In this study, application of high-amplitude, confined, pulsed AMF to a mouse model is explored with the goal to provide data for a concomitant efficacy study of heating i.v. injected magnetic nanoparticles. Methods: Thirty-seven female BALB/c athymic nude mice (5-8 weeks) were exposed to an AMF with frequency of 153 kHz, and amplitude (400-1,300 Oe), duration (1-20 minutes), duty (15-100%), and pulse ON time (2-1,200 seconds). Mice were placed in a water-cooled four-turn helical induction coil. Two additional mice, used as controls, were placed in the coil but received no AMF exposure. Tissue and core temperatures as the response were measured in situ and recorded at 1-second intervals. Results: No adverse effects were observed for AMF amplitudes of < or =700 Oe, even at continuous power application (100% duty) for up to 20 minutes. Mice exposed to AMF amplitudes in excess of 950 Oe experienced morbidity and injury when the duty exceeded 50%. Conclusion: High-amplitude AMF (up to 1,300 Oe) was well tolerated provided the duty was adjusted to dissipate heat. Results presented suggest that further tissue temperature regulation can be achieved with suitable variations of pulse width for a given amplitude and duty combination. These results suggest that it is possible to apply high-amplitude AMF (>500 Oe) with pulsing for a time sufficient to treat cancer tissue in which magnetic nanoparticles have been embedded."

SUMMARY OF THE INVENTION

In accordance with some applications of the present invention, nanoparticles are administered to a subject suffering from cancer, which typically includes one or more primary or metastatic solid tumors. The nanoparticles typically have the following characteristics:

the nanoparticles preferentially absorb energy transmitted toward the subject's body relative to absorption of the energy by tissue of the subject; and the nanoparticles heat the healthy tissue surrounding the cancerous tissue to a temperature up to a pre-defined temperature, e.g., 47-53 degrees C., such as 50 degrees C. The temperature is a self-regulating attribute of a phase-change material (PCM) component of the nanoparticles, such as described hereinbelow.

An energy transmission unit, typically an RF transmitter, is used to deliver electromagnetic (EM) energy to the nanoparticles and heat the nanoparticles to a temperature of up to the pre-defined temperature. The energy transmission unit is configured to transmit EM energy toward the subject's body, which is absorbed by the nanoparticles as heat, thereby causing the cancerous cells to become heated to the pre-defined temperature, leading to cancer cell death. The cell death occurs due to cancer cells' membrane sensitivity to temperatures above about 45 degrees C., reduced heat dissipation, and reduced heat capacity.

Typically, the energy transmitting unit, typically the RF transmitter, is configured to transmit the EM energy in a pulse train alternating between high power and low power (optionally, the low power is no power). Parameters of the pulses include duty cycle, power range, pulse duration, and pulse frequency.

The nanoparticles' energy absorption and energy storage, as latent heat, is higher for a pulse-train EM field than a constant, non-pulsed, field, when the average field power for the pulsed field and the constant field is equal. Thus, to achieve the same energy absorption rate by the nanoparticles, the pulsed field average power is less than the average power of a constant, non-pulsed field.

The lower average field power results in a substantial reduction in the patient's Specific Absorption Rate (SAR), together with keeping the maximum predefined temperature of the nanoparticles, which can potentially provide improved treatment efficacy. In experiments conducted by the inventors, use of the above-mentioned pulse train alternating between high and low power, reduced the body's SAR by about 10-15% compared to application of EM energy at a constant field.

There is therefore provided, in accordance with an application of the present invention, a system for use with a subject suffering from cancer that includes one or more primary or metastatic solid tumors, the system including:

nanoparticles including a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and a radiofrequency (RF) transmitter, which is configured to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion.

For some applications, the system is configured such that the nanoparticles release the stored energy from the PCM during an entirety of each low power phase of the pulse train.

For some applications, the RF energy transmitter is configured so that a strength of a magnetic field of the low power is 1 mT-5 mT, and a strength of the magnetic field of the high power is 8 mT-15 mT.

For some applications, the RF energy transmitter is configured to transmit the energy so that a ratio of a strength of the high power to a strength of the low power is 2-13.

For some applications, the pulse frequency is 1 Hz-2 Hz.

For some applications, the RF energy transmitter is configured so transmit the energy in the pulse train at an emitted energy modulation duty cycle of 25%-75%, the emitted energy modulation duty cycle being a ratio between operation time at high power and operation time at low power.

For some applications, the emitted energy modulation duty cycle is 30%-70%.

For some applications, the RF energy transmitter is configured to transmit the energy by transmitting a total emitted field power of 5-15 mT, the total emitted field power being the root mean square (RMS) of each of the pulses of the pulse train.

For some applications, the RF energy transmitter is configured to transmit the energy by generating an RF alternating magnetic field (AMF).

For some applications, the RF energy transmitter is configured to generate the RF AMF having a high frequency of 100 kHz-600 KHz.

For some applications, the at least a portion of the subject's body includes a torso of the subject's body, and the RF energy transmitter is configured to transmit the energy to the torso.

For some applications, the RF energy transmitter is configured to transmit the energy to an entirety of the torso.

For some applications, the RF energy transmitter includes a helical coil, which is sized and shaped so as to accommodate the at least portion a portion of the subject's body within the helical coil, and the RF energy transmitter is configured to transmit the RF energy to the at least a portion of the subject's body disposed within the helical coil.

For some applications, the nanoparticles preferentially absorb energy from the RF transmitter relative to tissue of the subject.

For some applications, the PCM layer includes an interior portion that (a) surrounds the magnetic metallic core and (b) is surrounded by an outer layer including poly (ethylene glycol) (PEG).

For some applications, the PEG has a molecular weight of 20,000 Dalton.

For some applications, the interior portion of the PCM layer includes a poloxamer.

For some applications, the poloxamer includes poloxamer 188.

For some applications, the magnetic metallic core includes a plurality of nanoparticle-cores coencapsulated in the PCM layer.

For some applications, the nanoparticle-cores include iron oxide.

For some applications, the nanoparticle-cores include superparamagnetic iron oxide oleic-acid capped superparamagnetic iron oxide ($Fe_3O_4$) nanoparticles (SPIONs).

For some applications, the phase change material includes paraffin wax including 24-hydrocarbon chains (tetracosane).

For some applications, the nanoparticles have an average hydrodynamic diameter of 90-165 nm.

For some applications:

the PCM layer includes an interior portion that (a) surrounds the magnetic metallic core and (b) is surrounded by an outer layer including poly (ethylene glycol) (PEG) having a molecular weight of 20,000 Dalton, the interior portion of the PCM layer includes poloxamer 188, the magnetic metallic core includes nanoparticle-cores coencapsulated in paraffin wax including 24-hydrocarbon chains (tetracosane), the nanoparticle-cores include superparamagnetic iron oxide oleic-acid capped superparamagnetic iron oxide ($Fe_3O_4$) nanoparticles (SPIONs), and the nanoparticles have an average hydrodynamic diameter of 90-165 nm.

There is further provided, in accordance with an application of the present invention, a method for treating a body of a subject suffering from cancer that includes one or more primary or metastatic solid tumors, the method including:

administering nanoparticles to the subject's body, each of the nanoparticles including a magnetic metallic core and a phase-change material (PCM) layer that surrounds the magnetic metallic core and includes a PCM that is configured to absorb latent heat of fusion, by undergoing a phase change selected from the group consisting of: solid to liquid, and gel to liquid, the phase-change occurring at a phase-change temperature of 42-80 degrees C.; and activating a radiofrequency (RF) energy transmitter to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion.

For some applications, the nanoparticles release the stored energy from the PCM during an entirety of each low power phase of the pulse train.

For some applications, activating the RF energy transmitter to emit the energy at low and high power per individual pulse cycle includes setting a strength of a magnetic field of the low power to be 1 mT-5 mT, and a strength of the magnetic field of the high power to be 8 mT-15 mT.

For some applications, activating the RF energy transmitter to emit the energy at low and high power per individual pulse cycle includes setting respective strengths of magnetic fields of the low power and the high power so that a ratio of the strength of the high power to the strength of the low power is 2-13.

For some applications, the pulse frequency is 1 Hz-2 Hz.

For some applications, activating the RF energy transmitter to transmit the energy includes setting an emitted energy modulation duty cycle to be 25%-75%, the emitted energy modulation duty cycle being a ratio between operation time at high power and operation time at low power.

For some applications, the emitted energy modulation duty cycle is 30%-70%.

For some applications, activating the RF energy transmitter to transmit the energy includes transmitting a total emitted field power of 5-15 mT, the total emitted field power being the root mean square (RMS) of each of the pulses of the pulse train.

For some applications, activating the RF energy transmitter to transmit the energy includes activating the RF energy transmitter to generate an RF alternating magnetic field (AMF).

For some applications, activating the RF energy transmitter to generate the RF AMF having a high frequency of 100 kHz-600 KHz.

For some applications, the at least a portion of the subject's body includes a torso of the subject's body, and activating the RF energy transmitter includes activating the RF energy transmitter to transmit the energy to the torso.

For some applications, activating the RF energy transmitter includes activating the RF energy transmitter to transmit the energy to an entirety of the torso.

For some applications, the RF energy transmitter includes a helical coil, the at least portion a portion of the subject's body is disposed within the helical coil, and activating the RF energy transmitter includes driving the helical coil to transmit the RF energy to the at least a portion of the subject's body disposed within the helical coil.

For some applications, the nanoparticles preferentially absorb energy from the RF transmitter relative to tissue of the subject.

For some applications, the PCM layer includes an interior portion that (a) surrounds the magnetic metallic core and (b) is surrounded by an outer layer including poly (ethylene glycol) (PEG).

For some applications, the PEG has a molecular weight of 20,000 Dalton.

For some applications, the interior portion of the PCM layer includes a poloxamer.

For some applications, the poloxamer includes poloxamer 188.

For some applications, the magnetic metallic core includes a plurality of nanoparticle-cores coencapsulated in the PCM layer.

For some applications, the nanoparticle-cores include iron oxide.

For some applications, the nanoparticle-cores include superparamagnetic iron oxide oleic-acid capped superparamagnetic iron oxide ($Fe_3O_4$) nanoparticles (SPIONs).

For some applications, the phase change material includes paraffin wax including 24-hydrocarbon chains (tetracosane).

For some applications, the nanoparticles have an average hydrodynamic diameter of 90-165 nm.

For some applications:

the PCM layer includes an interior portion that (a) surrounds the magnetic metallic core and (b) is surrounded by an outer layer including poly (ethylene glycol) (PEG) having a molecular weight of 20,000 Dalton, the interior portion of the PCM layer includes poloxamer 188, the magnetic metallic core includes nanoparticle-cores coencapsulated in paraffin wax including 24-hydrocarbon chains (tetracosane), the nanoparticle-cores include superparamagnetic iron oxide oleic-acid capped superparamagnetic iron oxide ($Fe_3O_4$) nanoparticles (SPIONs), and the nanoparticles have an average hydrodynamic diameter of 90-165 nm.

The present invention will be more fully understood from the following detailed description of embodiments thereof, taken together with the drawings, in which:

DETAILED DESCRIPTION OF EMBODIMENTS

The average field power in millitesla (mT) is defined as root mean square (RMS), which can be calculated using the following Equation A:

$$B[mT]_{RMS} = \lim_{T \to \infty} \sqrt{\frac{1}{2T} \int_{-T}^{T} f(t)^2 dt} \qquad \text{EQUATION A}$$

in which T=time period and $f$(t)=waveform function.

This calculation is performed for at least several full time periods.

Parasitic heating of a subject's body is measured by Specific Absorption Rate (SAR), which can be calculated using the following Equation B:

$$SAR = C \cdot r^2 \cdot B_{RMS}^2 \cdot f^2 \qquad \text{EQUATION B}$$

in which C=equation constant, r=Body radius [cm], $B_{RMS}$=EM field power [mT], and $f$=EM field frequency [kHz].

The following is an example of the pulsed average field power versus a constant field average power, in accordance with some applications of the present invention. Applying a constant 9 mT RMS field will produce a SAR of 81 W/kg versus applying a pulsed 8.51 mT RMS field, which yields a lower SAR of 72.4 W/kg. The ratio between the SAR results in an 11% reduction of the SAR in favor of the pulsed field modality. The pulsed field is step modulated between 1 mT low power and 12 mT high power at 1 Hz with a 50% duty cycle. For example, the average field strength value may be calculated using the following Equation C:

$$B_{rms} = \sqrt{\frac{1}{T_p} \left( \int_{0}^{t_1} B_{12mT}^2 dt + \int_{t_1}^{T_p} B_{1mT}^2 dt \right)} = 8.51 [mT] \qquad \text{EQUATION C}$$

The system typically generates an RF Alternating Magnetic Field (AMF), for example having a high frequency of 100 kHz to 600 KHz.

Figure 1:
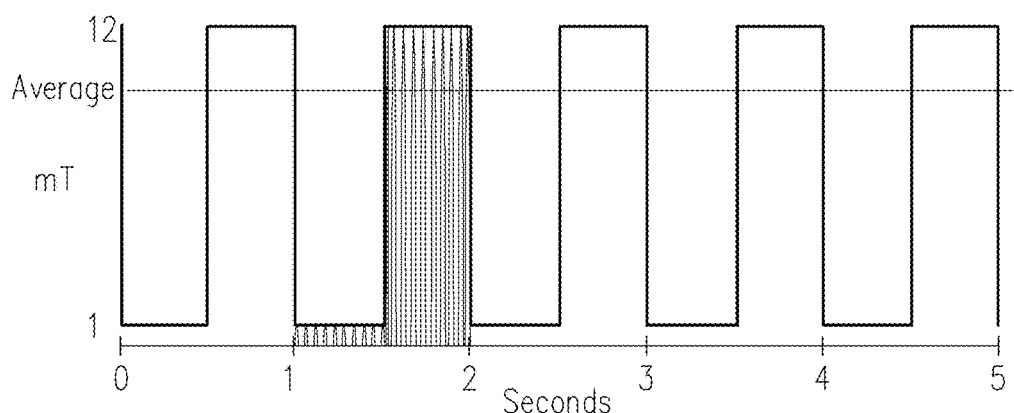
FIG. 1 is a schematic illustration of an exemplary pulse train alternating between high and low power, in accordance with an application of the present invention.

Reference is now made to FIG. 1, which is a schematic illustration of an exemplary pulse train, in accordance with an application of the present invention. This exemplary pulse train alternates between high power and low power (optionally, the low power is no power), having a 50% duty cycle, a 1 Hz frequency, and a power range of 1-12 mT. Typically, the AMF is applied at the same RF frequency during the pulse train, during both the high power and low power. In other words, the signal has a high-frequency component (which might be considered a carrier frequency) amplitude-modulated by a low-frequency component. (FIG. 1 shows the net power in mT of the AMF, which is inherently biphasic, because its field vector periodically reverses direction. FIG. 1 also highly illustratively shows the RF carrier frequency for one pulse cycle, at a frequency substantially lower than RF frequency, for the sake of illustration.)

Figure 2A:
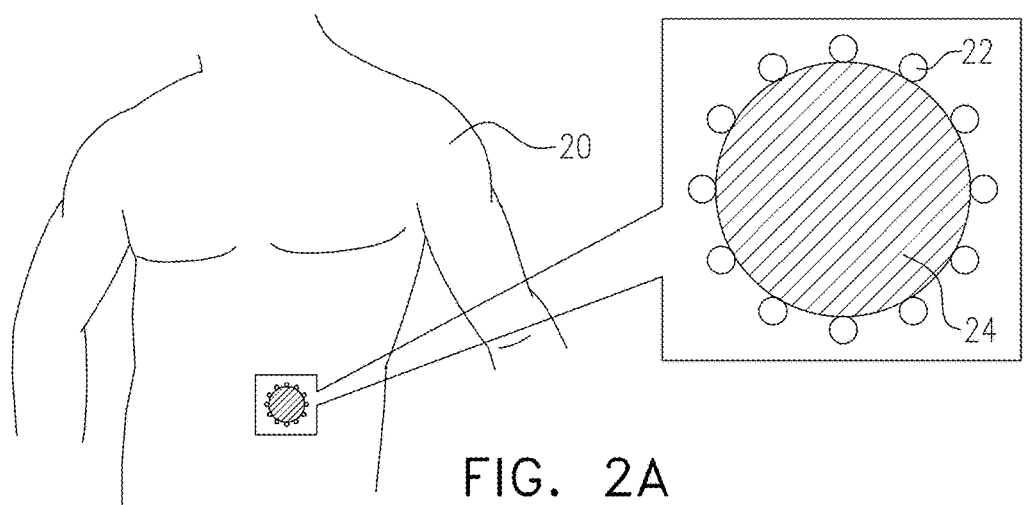
FIGS. 2A-B are schematic illustrations of a clinical RF system applied to a patient, after a plurality of nanoparticles have been administered to the subject and have become attached to a tumor that contains cancerous cells, in accordance with some applications of the present invention.
Figure 2B:
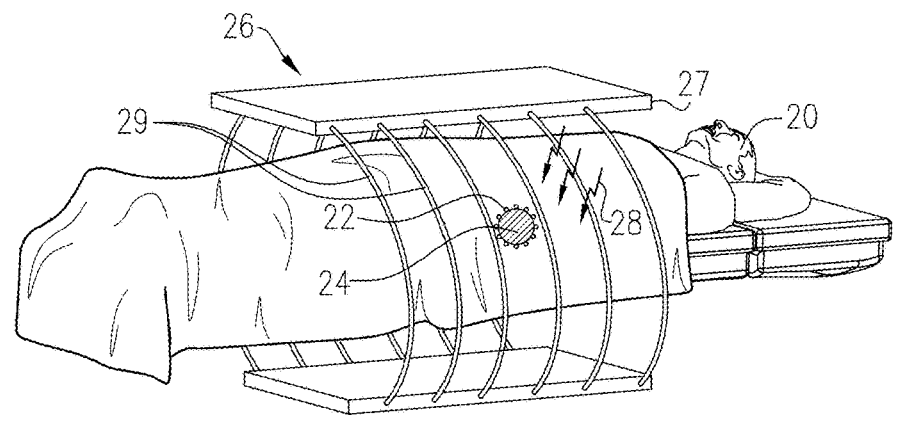

Reference is further made to FIGS. 2A-B, which are schematic illustrations of a subject 20 who is suffering from cancer, after a plurality of nanoparticles 22 have been administered to the subject (typically systemically, e.g., intravenously) and have accumulated at a tumor 24 that contains cancerous cells, in accordance with some applications of the present invention.

FIG. 2B is a sagittal cross-sectional view of an energy transmission unit 26 used after the administration of the nanoparticles to the subject. The energy transmission unit transmits energy (schematically 10 illustrated by arrows 28) toward the subject's body, causing at least some of the cancerous cells to become heated, such that the heated cells become injured or ruptured, leading to cell death. Energy transmission unit 26 typically comprises a helical coil 29, which, for example, surrounds all or a portion of the subject's torso.

Figure 3:
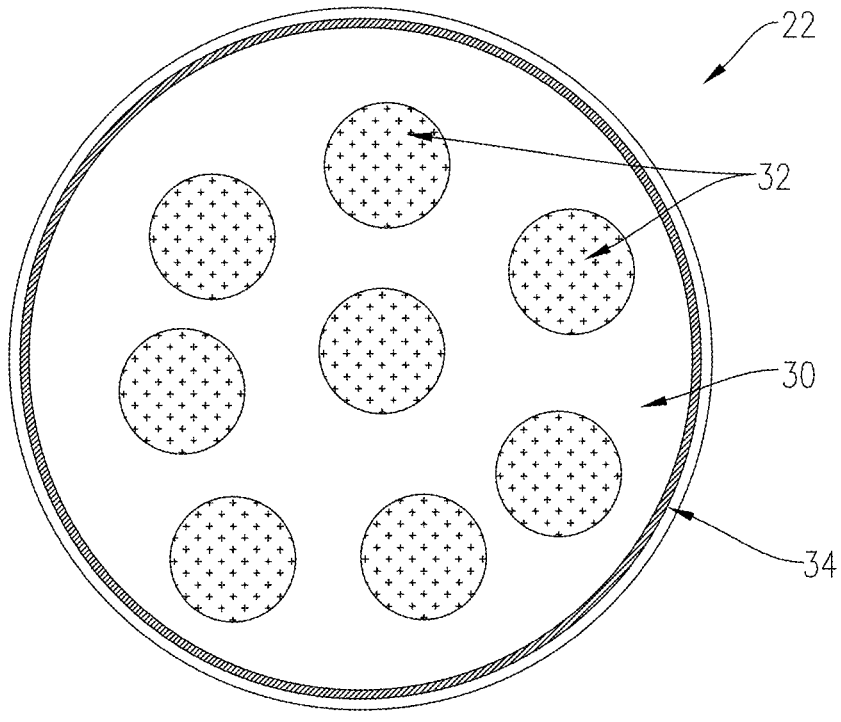
FIG. 3 is a schematic illustration of a cross-section of a nanoparticle, when, as shown for illustrative purposes, the nanoparticle has a spherical shape, in accordance with some applications of the present invention.

Reference is now made to FIG. 3, which is a schematic illustration of a cross-section of a nanoparticle 22, when, as shown for illustrative purposes, nanoparticle 22 has a spherical shape, in accordance with some applications of the present invention. Typically, nanoparticle 22 comprises a phase-change material (PCM) layer 30 surrounding a magnetic metallic core. For example, the magnetic metallic core may comprise iron oxide nanoparticle-cores 32 (PCM layer 30 may also be considered a shell.)

Figure 4:
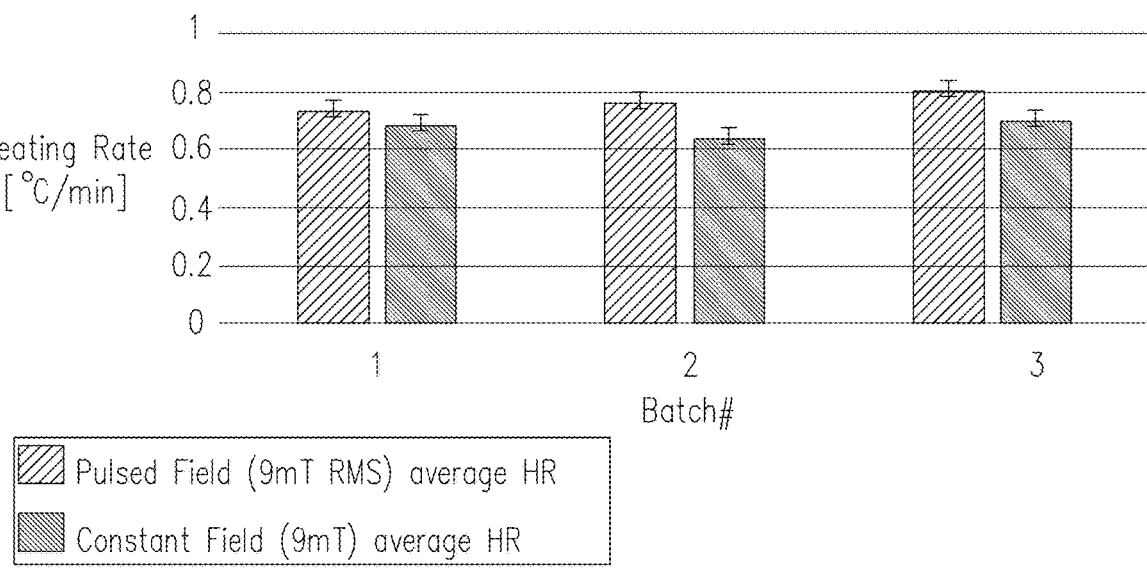
FIG. 4 is a graph showing the heating results of an experiment conducted using an experimental setup used to measure the heat energy emitted from the nanoparticles as a function of a pulse train field and of a constant field, in which various EM fields were transmitted to nanoparticles samples, in accordance with some applications of the present invention.

As described in detail hereinbelow, nanoparticles 22, shown in FIG. 3, may have one or more of the following characteristics:

the nanoparticles preferentially absorb energy transmitted toward the subject's body relative to absorption of the energy by tissue of the subject;

the nanoparticles prevent healthy tissues surrounding the cancerous tissues from being heated to a temperature that is greater than a pre-defined temperature (e.g., 47-53 degrees C., such as 50 degrees C.);

each of the nanoparticles comprise a core (e.g., or multi-core) of metal, such as iron oxide, which is heated by the EM magnetic field;

the nanoparticles comprise a PCM with self regulating temperature, such that absorbed RF energy at the predefined temperature will be stored as latent heat in the PCM;

the nanoparticles preferentially absorb, and store energy transmitted in pulses relative to absorption and storage of energy transmitted constantly; both the pulsing and the constant transmitted energies have the same RMS power average, such as described hereinbelow with reference to FIG. 4; and/or the nanoparticles release the stored energy from the PCM during an entirety of each low power phase of the pulse train.

In some applications of the present invention, nanoparticles 22 have one or more of the following characteristics.

For other applications, nanoparticles 22 have other characteristics. Thus, the following characteristics should be understood as only exemplary and not limiting. Alternatively or additionally, nanoparticles 22 may implement any of the techniques described in one or more of the publications and/or patents incorporated herein by reference, including, but not limited to, nanoparticles described in one or more of the following publications, all of which are incorporated herein by reference:

PCT Publication WO 2025/088597 to Kraus et al.

Kraus S et al., "Novel Nanoparticle-Based Cancer Treatment, Effectively Inhibits Lung Metastases and Improves Survival in a Murine Breast Cancer Model," Front Oncol. 2021 Nov. 5; 11:761045.

Kraus S et al., "Self-regulating novel iron oxide nanoparticle-based magnetic hyperthermia in swine: biocompatibility, biodistribution, and safety assessments," Arch Toxicol. 2022 September; 96(9):2447-2464.

For some applications, PCM layer 30 comprises an interior portion that (a) surrounds the magnetic metallic core and (b) is surrounded by an outer layer 34, e.g., comprising poly(ethylene glycol) (PEG). For some applications, the PEG has a molecular weight of 20,000 Dalton. For some applications, interior portion of PCM layer 30 comprises a poloxamer, e.g., comprising poloxamer 188.

For some applications, such as shown in FIG. 3, the magnetic metallic core comprises a plurality of nanoparticle-cores 32 coencapsulated in PCM layer 30. For some of these applications, nanoparticle-cores 32 comprise iron oxide. For example, nanoparticle-cores 32 may comprise superparamagnetic iron oxide oleic-acid capped superparamagnetic iron oxide ($Fe_3O_4$) nanoparticles (SPIONs).

For some applications, the PCM comprises paraffin wax comprising 24-hydrocarbon chains (tetracosane).

For some applications, nanoparticles 22 have an average hydrodynamic diameter of 90-165 nm.

For some applications, energy transmission unit 26, as shown in FIG. 2B, with which the nanoparticles are used, is an RF transmitter. FIG. 2B shows a cross-section of the patient's body inside the energy transmission unit. The energy transmission unit (e.g., the RF transmitter) may comprise a housing 27 that is shaped like an MRI scanner, such that the entire body of the subject, or a portion of the subject's body (e.g., the subject's torso (e.g., an entirety or a portion of the torso), as shown) is disposed inside the housing. Helical coil 29 (a cross-section of which is shown in FIG. 2B) spirals around inside the housing and transmits energy in the general direction of the subject's body. As used in the present application, including in the claims, the torso of the patient's body means the central part of the body that includes the chest, abdomen, and pelvis, but excludes the head and neck.

Alternatively or additionally, energy transmission units may include respective transmission and receiving electrode coils, such as shown in FIG. 2B (e.g., helix coil plates), which are disposed on opposite sides of the subject's body (e.g., above and below the subject's body or on body sides). For such applications, the energy transmission unit is typically configured to generate an EM field that passes through at least a portion of the subject's body, by transmitting EM energy from the transmission electrode to the receiving electrode.

Reference is again made to FIG. 1. For some applications, energy transmission unit 26 is configuration to transmit energy in a pulse train, typically have one or more of the following characteristics and exemplary values:

the emitted energy (the magnetic field of the system's output) is bound by a defined power range (system input), the emitted energy is defined as low and high field power per individual pulse cycle. For example, the low-power magnetic field may have a strength of at least 1 mT, no more than 7 mT (e.g., no more than 5 mT), and/or 1 mT-7 mT, e.g., 1 mT-5 mT, and/or the high-power magnetic field may have a strength of at least 8 mT, no more than 15 mT, and/or 8 mT-15 mT Alternatively, no energy may be emitted instead of the low-power portion of each pulse cycle;

the emitted energy (the magnetic field of the system's output) is bound by a defined power range (system input), the emitted energy is defined as low and high field power per individual pulse cycle. For example, a ratio of a strength of the high-power magnetic field to a strength of the low-power magnetic field may be at least 2, no more than 15 (e.g., no more than 13), and/or 2-15, e.g., 2-13;

the emitted energy number of pulses per second (pulse frequency) may be measured in Hz; for example, the pulse frequency may be at least 1 Hz, no more than 5 Hz (e.g., no more than 2 Hz), and/or 1-5 Hz (e.g., 1-2 Hz), such as 1 Hz, 2 Hz, or 5 Hz; alternatively, the pulse frequency is 0.5 Hz-5 Hz, such as 0.5 Hz-2 Hz; the pulse frequency is also known as the pulse repetition frequency, and is the reciprocal of the length of one complete cycle (each complete cycle incudes a high-power phase and a low-power phase);

the emitted energy modulation duty cycle is defined as the ratio between the operation time at high power and the operation time at low power; the duty cycle can change from cycle to cycle or remain constant across the cycles; the duty cycle may vary at any range between 1% and 99%, typically a duty cycle of 25%-75%, such as 30%-70%, e.g., 50%, is applied; for example, if the pulse frequency is 1 Hz and the duty cycle is 30%, the length of a complete cycle is 1 second, which includes 300 milliseconds at high power and 700 milliseconds at low power;

the length of the high-power phase of each cycle is at least 0.1 seconds, such as at least 0.33 seconds or at least 0.5 seconds; no more than 2 seconds, such as no more than 1.5 seconds, no more than 1 second, no more than 0.75 seconds, or no more than 0.5 seconds; and/or 0.1-2 seconds, e.g., 0.33 seconds-2 seconds, or 0.33 seconds-1 second, e.g., 0.33-0.75 seconds;

the length of the low-power phase of each cycle is at least 0.1 seconds, such as at least 0.33 seconds or at least 0.5 seconds; no more than 2 seconds, such as no more than 1.5 seconds, no more than 1 second, no more than 0.75 seconds, or no more than 0.5 seconds; and/or 0.1-2 seconds, e.g., 0.33 seconds-2 seconds, or 0.33 seconds-1 second, e.g., 0.33-0.75 seconds; and/or the total emitted field power is defined as the RMS average of the pulse; this RMS average is the value that is used to calculate the SAR on the patient, such as using Equation B, described hereinabove. For example, the total emitted field power may be 5-15 mT.

The relatively short lengths of the high-power phase of the cycle described immediately above, particularly those lengths no more than 1 second, generally result in less heating of the patient's tissue than if longer high-power phases were used. In addition, the relatively short lengths of the low-power phase of the cycle described immediately above generally result in continuous heating (i.e., continuous treatment) of the cancerous tissue because the heat stored in the PCM of the nanoparticles during the high-power phase of each cycle is released throughout the following low-power phase. By contrast, conventional nanoparticles that comprise a magnetic material (e.g., iron oxide), but do not comprise a PCM, would typically generate a therapeutically meaningful amount of heat only during RF energy transmission (typically substantially higher temperatures than 50 degrees C.), and quickly cool during low-power or OFF phase of the cycle because conventional nanoparticles store little or no energy during the ON phase of the cycle.

For some applications, the pulses are rectangular (but not necessarily perfectly rectangular because of constraints of the transmitter, such as the rise time and the fall time, which may result in slightly non-rectangular pulse edges). Alternatively, the pulses are non-rectangular, such as sinusoidal.

Alternatively, or additionally, the operation mode of the energy transmission unit is a constant mode, in which the transmitted energy is delivered constantly and typically has one or more of the following characteristics:

the emitted energy has a defined constant power output, and the constant power does not vary within the nanoparticles' latent heat and phase-change time;

the total emitted power is defined as the RMS average of the power output; this RMS average, as described with reference to Equation A, is the value that is used to calculate the SAR on the patient, such as using Equation B, described hereinabove; and/or the emitted energy average field power is the value that sets the patient SAR, such as using Equation C, described hereinabove.

Figure 5A:
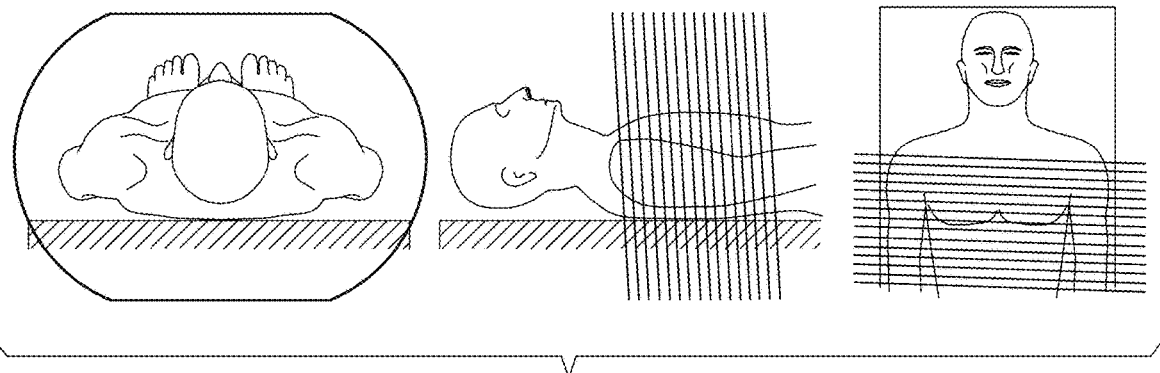
FIGS. 5A-C illustrate a mathematical simulation performed by the inventors, in accordance with some applications of the present invention.
Figure 5B:
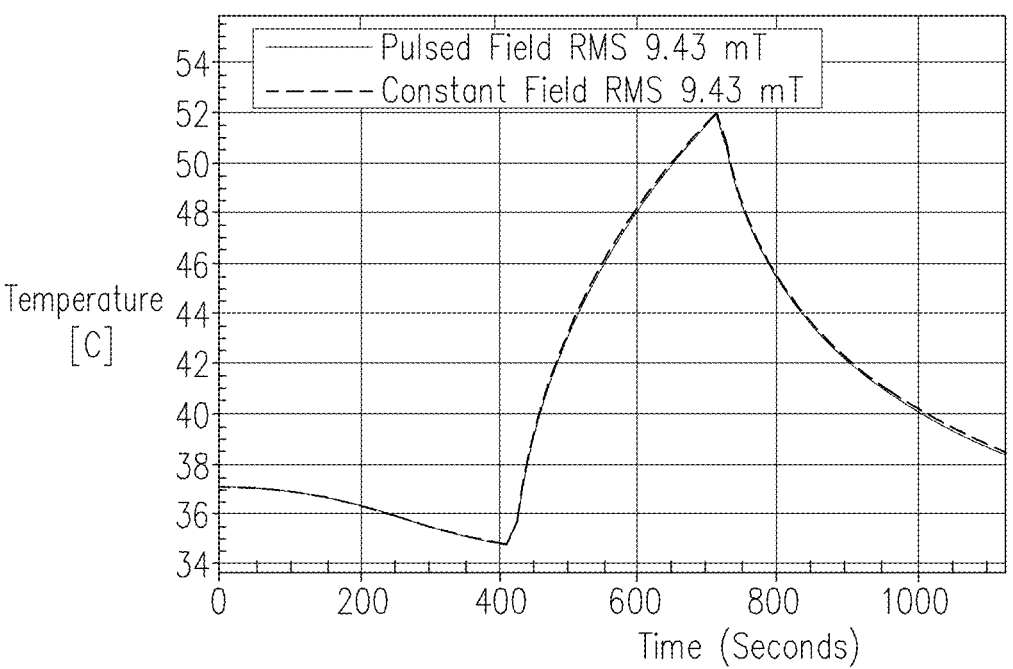
Figure 5C:
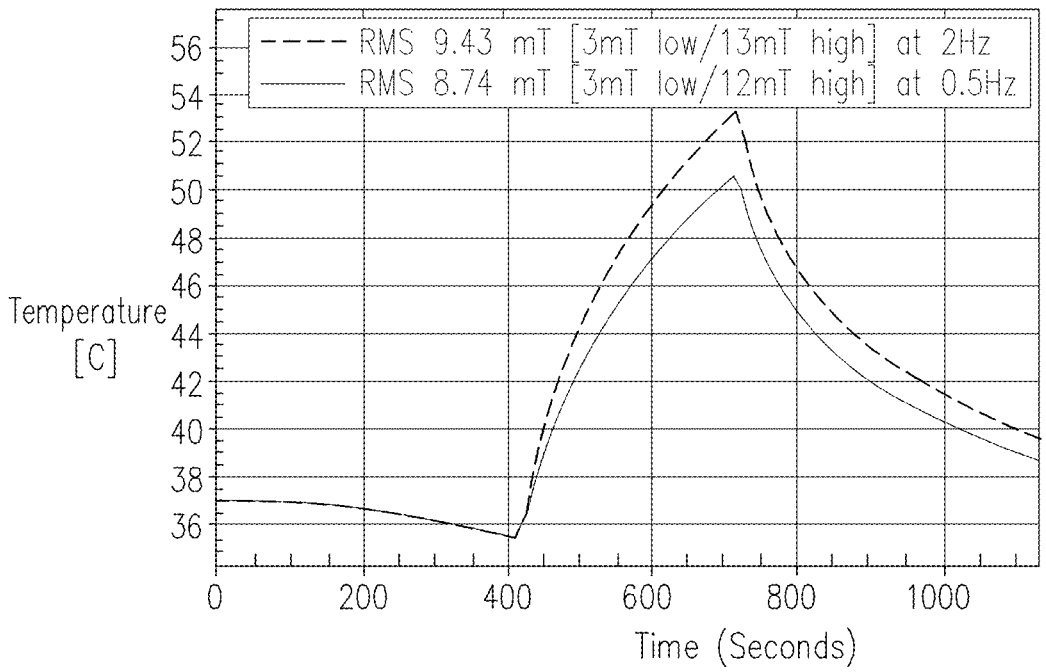

Reference is now made to FIGS. 5A-C, which illustrates a mathematical simulation performed by the inventors using some techniques of the present invention. FIG. 5A includes three diagrams of a simulated patient body inside a helical coil, in three respective views.

As is known in physics, energy transmitted toward a subject's body is partly absorbed by the subject's body according to Faraday's law of induction and creates eddy currents that can cause unwanted heating of tissue regardless of the presence of the nanoparticles. This absorbed energy is commonly known as body SAR and is proportional to the root mean square of the energy average power (RMS).

FIG. 5B is a graph showing a mathematically simulated tissue heating profile for the modeled patient of FIG. 5A, in accordance with an application of the present invention. The graph shows the temperature versus time of a 5-minute (300-second) irradiation cycle (from time 400 seconds to time 700 seconds in the graph) for a pulsed EM field, in accordance with an application of the present invention, and a constant EM field. The pulsed EM field and constant EM field were modeled to have the same RMS of 9.43 mT. As can be seen, the pulsed EM field and constant EM field resulted in nearly exactly the same mathematically simulated patient SAR. (Based on additional modeling, the inventors believe that the differing frequencies between the two signals shown in FIG. 5B do not materially affect the modeled SAR.)

FIG. 5C is another graph showing a mathematically simulated tissue heating profile for the modeled patient of FIG. 5A, in accordance with an application of the present invention. The graph shows the temperature versus time of a 5-minute (300-second) irradiation cycle (from time 400 seconds to time 700 seconds in the graph) for two different pulsed EM fields, in accordance with an application of the present invention. The two pulsed EM fields were modeled to have different average RMS values: an RMS of 9.43 mT and an RMS of 8.74 mT. As can be seen in the graph of FIG. 5C, the pulsed field having the lower average RMS resulted in lower modeled tissue heating, reflecting lower patient SAR. Thus, based on this mathematical modeling, a lower average RMS results in a lower body SAR.

The mathematical stimulation described immediately above further included calculation of CEM43 values for tissues exposed to EM fields having differing RMS. As known in the art, CEM43 is a thermal dose parameter that converts heat exposure over time into an equivalent number of minutes at 43° C., used to predict cell death and tissue damage. As can be seen in Table 1, lower RMS values result in substantially lower calculated CEM43 values, including for the reduction from 9.43 to 8.74 RMS, corresponding to the reduction in RMS of the pulsed field compared to the constant field illustrated in FIG. 5C. This exemplary reduction in RMS provides an 86% reduction in CEM43.

TABLE 1

| Field power in RMS | CEM43 at 300 seconds |
| --- | --- |
| 9.43 | 55,141 |
| 8.74 | 8,054 |
| 8.04 | 1,262 |
| 7.3 | 224 |

Reference is made to FIG. 4 and FIGS. 5A-C. These two experiments, taken together, demonstrate that the use of the pulsed field technique described herein may reduce the SAR by about 10-15% compared to a constant field, and yet still achieve the higher heating rate of the nanoparticles compared to heating rate achieved using a constant field. The higher rate of heating rate of the nanoparticles with the two types of fields is due to the PCM and latent heat energy storage properties of the nanoparticles.

An experiment was performed in humans using some techniques of the present invention. In the experiment, four human subjects, three males and one female, were administered the nanoparticles described in PCT Publication WO 2025/088597 to Kraus et al., at doses of 0.6, 1.2 and 1.8 mg/kg. About four hours after administration of the nanoparticles, the subjects were irradiated with one of the following two types of EM fields:

pulsed-field experimental group—two of the subjects (one male and one female—a pulse train EM field alternating between a high power of 11.5 mT and a low power of 1 mT resulting in an average field strength of 8.2 mT RMS; and constant-field experimental group—two of the subjects (two males)—a constant EM field having a power of 9.5 mT RMS.

Both the pulsed EM field and the constant EM field were applied at an RF frequency of 278 kHz, for 3 intervals of 5 minutes each, with 5-minute breaks between each interval.

During both types of RF AMF application, the subjects' oral temperature was measured at the beginning and at the end of each irradiation cycle. Following irradiation, the subjects completed a comfort/pain questionnaire.

The following Tables 2 and 3 show the recorded oral (core) temperature changes for the pulsed-field irradiated group and the constant-field irradiated group, respectively:

TABLE 2

| | | Pulsed Field | | |
| Patient | Weight | AMF start temp. | AMF end temp. | Temp. change at treatment |
| --- | --- | --- | --- | --- |
| #1 | 53 Kg | 37.1° C. | 36.8° C. | −0.3° C. |
| #2 | 58.3 Kg | 37.0° C. | 37.1° C. | +0.1° C. |

TABLE 3

| | | Contant Field | | |
| Patient | Weight | AMF start temp. | AMF end temp. | Temp. change at treatment |
| --- | --- | --- | --- | --- |
| #3 | 50 Kg | 36.6° C. | 37.3° C. | +0.7° C. |
| #4 | 57 Kg | 36.9° C. | 37.2° C. | +0.3° C. |

The results indicate that:

oral (i.e., core) temperatures remained within physiological range at the end of AMF irradiation without substantial changes compared to the temperatures measured at start of AMF. Temperature changes between start and end of AMF were minimal and less than 1 degree C. (up to 0.7° C. in patient 3 irradiated at a constant field).

the temperature data shows that the temperature change was less than 0.8° C. for all subjects' averages, and the total temperature change average of all the subjects was 0.2° C. This indicates that the low temperature rise is caused by the lower RMS field strength of the EM field.

the oral temperature of the two subjects irradiated with a pulsed train field did not change and was even slightly reduced indicating on a controlled subject core temperature.

the pain grade was 2 (i.e., moderate), meaning that the subjects were capable of enduring pulse train irradiation for 3 sessions of five minutes irradiation cycles; this also indicates that longer pulse train cycles are feasible for better treatment efficacy.

the Net Forward pulse train Power of 14.5 KW is lower by 13% than the Net Forward constant Power of 16.5 kW. This transmitted power reduction results in the lowering the subjects' SAR as expected. In particular, using Equation B above, the calculated SAR is 24% lower when the field has 13% less field power $(1-0.872^2)$.

In conclusion, embodiments of the present invention provide a pulsed train mode of EF AMF irradiation for use with nanoparticle treatment of cancer. In contrast to a treatment mode applied with a constant power field, the pulsed train mode generally lowers the subject's SAR, improves the subject's treatment tolerability in terms of heat sensation and potential pain in hot spots, while enabling better therapeutic efficacy.

The thermal simulation modeling using an anatomical human model, described hereinabove with reference to FIGS. 5A-C, demonstrates that the subject's SAR is dependent on the average RMS. In addition, the nanoparticles showed a higher heating rate under a pulse train field compared to a constant field for the same RMS value, as described hereinabove with reference to FIG. 4.

The clinical study results described hereinabove demonstrate the safety and the potential treatment efficacy improvement of the pulse train irradiation mode compared to the constant irradiation mode. Use of a pulsed field, rather than a constant field, often allows the application of longer uninterrupted irradiation periods (e.g., at least 3 minutes, such as at least 5 minutes), without the need to stop irradiation before the completion of the period because of patient pain and/or tissue overheating. Heating the cancerous cells in complete, uninterrupted periods of at least 3 minutes, e.g., at least 5 minutes, is more effective at killing cancerous cells than applying the same total duration of heating in shorter periods with breaks, resulting in greater treatment efficacy. In addition, application of a pulse train allows the use of a lower average field power, while preserving treatment time and nanoparticle heating, and therefore efficacy.

It will be appreciated by persons skilled in the art that the present invention is not limited to what has been particularly shown and described hereinabove. Rather, the scope of the present invention includes both combinations and sub combinations of the various features described hereinabove, as well as variations and modifications thereof that are not in the prior art, which would occur to persons skilled in the art upon reading the foregoing description.

In an embodiment, the methods and therapeutic combinations described herein are combined with methods and therapeutic combinations described in one or more of the following publications, which are incorporated herein by reference:

U.S. Pat. No. 9,872,902 to Hof et al.
US Patent Application Publication 2020/0054886 to Hof
U.S. Provisional Patent Application 63/545,817, filed Oct. 26, 2023
PCT Publication WO 2025/088597 to Kraus et al.
U.S. Provisional Patent Application 63/705,326, filed Oct. 9, 2024
Kraus S et al., "Novel Nanoparticle-Based Cancer Treatment, Effectively Inhibits Lung Metastases and Improves Survival in a Murine Breast Cancer Model," Front Oncol. 2021 Nov. 5; 11:761045
Kraus S et al., "Self-regulating novel iron oxide nanoparticle-based magnetic hyperthermia in swine: biocompatibility, biodistribution, and safety assessments," Arch Toxicol. 2022 September; 96(9):2447-2464

In case of conflict between definitions provided herein and those provided in the publications incorporated herein by reference, the definitions provided herein will prevail.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system for use with a subject suffering from cancer that includes one or more primary or metastatic solid tumors, the system comprising:
    nanoparticles comprising a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and
    a radiofrequency (RF) transmitter, which is configured to transmit energy, in a pulse train alternating between high power and low power at a pulse frequency of 1 Hz -5 Hz, to at least a portion of the subject's body, so that the nanoparticles are heated to the phase-change temperature of the PCM, and store energy from the pulse train in the PCM as latent heat of fusion,
    wherein the RF energy transmitter is configured so that a strength of a magnetic field of the low power is 1 mT-5 mT, and a strength of the magnetic field of the high power is 8 mT-15 mT.

2. The system according to claim 1, wherein the system is configured such that the nanoparticles release the stored energy from the PCM during an entirety of each low power phase of the pulse train.

3. The system according to claim 1, wherein the pulse frequency is 1 Hz-2 Hz.

4. The system according to claim 1, wherein the RF energy transmitter is configured to transmit the energy by generating an RF alternating magnetic field (AMF).

5. The system according to claim 4, wherein the RF energy transmitter is configured to generate the RF AMF having a high frequency of 100 kHz-600 kHz.

6. The system according to claim 1, wherein the at least a portion of the subject's body includes a torso of the subject's body, and wherein the RF energy transmitter is configured to transmit the energy to the torso.

7. The system according to claim 1, wherein the RF energy transmitter comprises a helical coil, which is sized and shaped so as to accommodate the at least a portion of the subject's body within the helical coil, and wherein the RF energy transmitter is configured to transmit the RF energy to the at least a portion of the subject's body disposed within the helical coil.

8. The system according to claim 1, wherein the nanoparticles preferentially absorb energy from the RF transmitter relative to tissue of the subject.

9. The system according to claim 1, wherein the PCM layer comprises an interior portion that (a) surrounds the magnetic metallic core and (b) is surrounded by an outer layer comprising poly (ethylene glycol) (PEG).

10. The system according to claim 1, wherein the magnetic metallic core comprises a plurality of nanoparticle-cores coencapsulated in the PCM layer.

11. The system according to claim 10, wherein the nanoparticle-cores comprise iron oxide.

12. The system according to claim 10, wherein the phase change material comprises paraffin wax comprising 24-hydrocarbon chains (tetracosane).

13. The system according to claim 1, wherein the nanoparticles have an average hydrodynamic diameter of 90-165 nm.

14. A system for use with a subject suffering from cancer that includes one or more primary or metastatic solid tumors, the system comprising:
    nanoparticles comprising a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and
    a radiofrequency (RF) transmitter, which is configured to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion, wherein the RF energy transmitter is configured to transmit the energy so that a ratio of a strength of the high power to a strength of the low power is 2-13.

15. The system according to claim 14, wherein the system is configured such that the nanoparticles release the stored energy from the PCM during an entirety of each low power phase of the pulse train.

16. The system according to claim 14, wherein the pulse frequency is 1 Hz-2 Hz.

17. A system for use with a subject suffering from cancer that includes one or more primary or metastatic solid tumors, the system comprising:

nanoparticles comprising a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and a radiofrequency (RF) transmitter, which is configured to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion, wherein the RF energy transmitter is configured so transmit the energy in the pulse train at an emitted energy modulation duty cycle of 25%-75%, the emitted energy modulation duty cycle being a ratio between operation time at high power and operation time at low power.

18. The system according to claim 17, wherein the RF energy transmitter is configured so that a strength of a magnetic field of the low power is 1 mT-5 mT, and a strength of the magnetic field of the high power is 8 mT-15 mT.

19. A system for use with a subject suffering from cancer that includes one or more primary or metastatic solid tumors, the system comprising:

nanoparticles comprising a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and a radiofrequency (RF) transmitter, which is configured to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion, wherein the RF energy transmitter is configured to transmit the energy by transmitting a total emitted field power of 5-15 mT, the total emitted field power being the root mean square (RMS) of each of the pulses of the pulse train.

20. A system for use with a subject suffering from cancer that includes one or more primary or metastatic solid tumors, the system comprising:

nanoparticles comprising a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and a radiofrequency (RF) transmitter, which is configured to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion, wherein the PCM layer comprises an interior portion that (a) surrounds the magnetic metallic core and (b) is surrounded by an outer layer comprising poly (ethylene glycol) (PEG), and wherein the interior portion of the PCM layer comprises a poloxamer.

21. A system for use with a subject suffering from cancer that includes one or more primary or metastatic solid tumors, the system comprising:

nanoparticles comprising a magnetic metallic core and a phase-change material (PCM) that surrounds the magnetic metallic core and is configured to absorb latent heat of fusion by undergoing a phase change selected from the group consisting of: solid to liquid, and gel to liquid, the phase-change occurring at a phase-change temperature of 42-80 degrees C.; and a radiofrequency (RF) transmitter, which is configured to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion, wherein the PCM layer comprises an interior portion that (a) surrounds the magnetic metallic core and (b) is surrounded by an outer layer comprising poly (ethylene glycol) (PEG) having a molecular weight of 20,000 Dalton, wherein the interior portion of the PCM layer comprises poloxamer 188, wherein the magnetic metallic core comprises nanoparticle-cores coencapsulated in paraffin wax comprising 24-hydrocarbon chains (tetracosane), wherein the nanoparticle-cores comprise superparamagnetic iron oxide oleic-acid capped superparamagnetic iron oxide ($Fe_3O_4$) nanoparticles (SPIONs), and wherein the nanoparticles have an average hydrodynamic diameter of 90-165 nm.

22. A method for treating a body of a subject suffering from cancer that includes one or more primary or metastatic solid tumors, the method comprising:

administering nanoparticles to the subject's body, each of the nanoparticles including a magnetic metallic core and a phase-change material (PCM) layer that surrounds the magnetic metallic core and includes a PCM that is configured to absorb latent heat of fusion, by undergoing a phase change selected from the group consisting of: solid to liquid, and gel to liquid, the phase-change occurring at a phase-change temperature of 42-80 degrees C.; and activating a radiofrequency (RF) energy transmitter to transmit energy, in a pulse train alternating between high power and low power at a pulse frequency of 1 Hz-5 Hz, to at least a portion of the subject's body, so that the nanoparticles are heated to the phase-change temperature of the PCM, and store energy from the pulse train in the PCM as latent heat of fusion, wherein activating the RF energy transmitter to emit the energy at low and high power per individual pulse cycle comprises setting a strength of a magnetic field of the low power to be 1 mT-5 mT, and a strength of the magnetic field of the high power to be 8 mT-15 mT.

\* \* \* \* \*